US00PP17769P3

(12) United States Plant Patent
Kordes

(10) Patent No.: US PP17,769 P3
(45) Date of Patent: May 29, 2007

(54) SHRUB ROSE PLANT NAMED 'KORUTELI'

(50) Latin Name: *Rosa hybrida*
Varietal Denomination: KORuteli

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 11/255,054

(22) Filed: Oct. 19, 2005

(65) Prior Publication Data

US 2007/0089204 P1 Apr. 19, 2007

(51) Int. Cl.
*A01H 5/00* (2006.01)

(52) U.S. Cl. ..... Plt./103

(58) Field of Classification Search ..... Plt./103
See application file for complete search history.

(56) References Cited

PUBLICATIONS

QZ (CPVO) Application # 2004/1682 Sep. 15, 2005 W. Kordes' Söhne.

*Primary Examiner*—Kent Bell
*Assistant Examiner*—June Hwu

(57) ABSTRACT

A new and distinct variety of rose with long lasting, novel cream white flowers, and attractive foliage with good disease resistance. It exhibits uniform upright and bushy growth with abundant flowers. The new variety propagates well using traditional methods. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORuteli'.

BACKGROUND OF THE INVENTION

The new variety of rose plant of the present invention originated from a controlled crossing in a breeding program of two distinct parents during the summer of 1992. The crossing was between 'Banzai 83', a non-patented rose and 'un-named seedling' of the breeding program of the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORuteli'.

SUMMARY OF THE INVENTION

The new rose plant may be distinguished from its seed parent, 'Banzai 83', by the following combination of characteristics:

1. The flowers of the seed parent have 35–40 petals while the flowers of the instant variety have 80–90 petals; and
2. the seed parent is of the hybrid tea class and has yellow flowers with red margins while 'KORuteli' is a shrub rose with cream white flowers.

The new rose plant may be distinguished from its pollen parent, an un-named seedling by the following combination of characteristics:

1. The flowers of the pollen parent are small while the flowers of the instant variety are large; and
2. The flowers of the pollen parent are single while the while the flowers of the instant variety are very double.

The objective of the hybridization was to create a new and distinct rose plant with unique qualities, such as:

1. Compact and uniform growth and flowering;
2. Abundant attractive, recurrent cream white flowers;
3. Attractive and abundant foliage; and
3. Resistance to diseases encountered in landscapes and gardens.

This combination of qualities is not present in prior rose cultivars. These objectives have been substantially achieved and in that distinguish 'KORuteli' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORuteli' was selected in July, 1993 from the seedling beds to be asexually propagated for further evaluation. The first asexual propagation of 'KORuteli' was done by budding to seedling understocks in July, 1993 at the W. Kordes Söhne Nursery in Offenseth-Sparrieshoop, Germany.

This initial and other subsequent propagations conducted in controlled environments show that the foregoing and all other characteristics of 'KORuteli' come true to form and are transmitted through succeeding generations.

BRIEF DESCRIPTION OF THE DRAWING

The accompanying color illustration shows as true as is reasonably possible to obtain in color photographs of this type, the typical characteristics of the buds, flowers, leaves, and stems of 'KORuteli'. Specifically illustrated in SHEET ONE Tight bud, bud with sepals dropped, and fully opened flower bloom;

Dissected flower with sepals attached;

Stem exhibiting thorns; and

Two leaves.

DETAILED BOTANICAL DESCRIPTION

The following is a description of 'KORuteli', as observed in its growth in September, 2005 in a nursery in Jackson County, Oreg. on plants of 2 years of age. Color references are made using The Royal Horticultural Society (London, England) Colour Chart, 2001 except where common terms of color are used.

For a comparison, several physical characteristics of the rose variety 'KORgretaum', a rose variety from the same inventor described and illustrated in U.S. Plant patent application Ser. No. 11/071,751 filed on Mar. 2, 2005 are compared to 'KORuteli' in Chart 1.

CHART 1

| Characteristic | 'KORuteli' | 'KORgretaum' |
|---|---|---|
| Flower bud color | Orange Group 27D | White Group 155C with intonations of Yellow-Green Group 149C. |
| Flower buds per stem | Multiple buds, with 9–12 stem. | Multiple buds with 4–10 per stem. |
| Length of prickles on the stems. | Average length 5–7 mm. | Average length 11–13 mm. |

Parents:

*Seed parent.*—'Banzai 83'.

*Pollen parent.*—'An un-named seedling'.

Classification:

*Botanical classification.*—*Rosa hybrida*, 'KORuteli'.

*Commercial classification.*—Shrub rose.

FLOWER AND FLOWER BUD

Blooming habit: Recurrent.

Flower bud:

*Size.*—Upon opening, 35–40 mm in length from base of receptacle to end of bud. Average diameter: 20 mm.

*Bud form.*—Long. Pointed ovoid.

*Bud color.*—As sepals first unfold, bud color is Orange Group 27D. Some buds with intonations of Red 54B on outermost petals. When ¼ open, the bud color is Orange-White Group 159A. Basal zone of outermost petals is Yellow Green Group 145C.

*Sepals.*—Size: Average 20 mm long×10 mm wide. Shape: Weak foliaceous appendages on three of the five sepals. Sepal apex is cirrose. Base is flat at union with receptacle. Quantity: Five. Surface texture: Upper surface: Slight to no pubescence. Lower surface: Slight to no pubescence. A few stipitate glands are present. Color: Upper surface Green Group 138B to Green Group 138C. Basal area of upper surface with intonations of Greyed-Red Group 182B. Lower surface Green Group 144B.

Receptacle:

*Surface.*—Smooth.

*Color.*—Green Group 144B.

*Shape.*—Urn shaped.

*Size.*—10 mm (h)×10 mm (w).

Peduncle:

*Surface.*—Smooth.

*Length.*—30–40 mm length.

*Diameter.*—2.0–3.0 mm average diameter.

*Color.*—Green Group 138A. Intonations of Greyed-Red Group 182B.

*Strength.*—Strong.

*Borne.*—Multiple flower buds per stem, generally 9 to 12.

Flower bloom:

*Fragrance.*—Light floral fragrance.

*Duration.*—On the plant 6–8 days. Senesced petals drop away cleanly.

*Size.*—Medium flowered garden rose. Average flower diameter is 70 mm when open. Range of diameters are 60 to 85 mm.

*Form.*—Shape of flower when viewed from the side: Upon opening, upper part: Convex. Upon opening, lower part: Flattened convex. Open flower, upper part: Flat. Open flower, lower part: Flat to flattened convex.

Color:

*Upon opening, petals.*—Outermost petals: Outer Side: Orange-White Group 159D. Inner Side: Orange-White Group 159D. Innermost petals: Outer Side: Orange-White Group 159C. Inner Side: Orange-White Group 159C.

*Upon opening, basal petal spots.*—Basal petal spot, outermost petals: Outer Side: Green-Yellow Group 1D. Inner Side: Green-Yellow Group 1D. Basal petal spot, innermost petals: Outer Side: Green-Yellow Group 2D. Inner Side: Green-Yellow Group 2D.

*After opening, petals.*—Outermost petals: Outer Side: Yellow-White Group 158C. Inner Side: Yellow-White Group 158C. Innermost petals: Outer Side: Yellow Orange Group 159D. Inner Side: Yellow Orange Group 159D.

*After opening, basal petal spots.*—Basal petal spot, outermost petals: Outer Side: Green-Yellow Group 1D. Inner Side: Green-Yellow Group 1D. Basal petal spot, innermost petals: Outer Side: Green-Yellow Group 1D. Inner Side: Green-Yellow Group 1D. Variegations: None.

General tonality: On open flower Yellow-White Group 158D. No change in the general tonality at the end of the fourth day. Afterwards, general tonality is White Group N155D.

Petals:

*Petal count.*—Very double. Approximately 75–80 petals under normal conditions.

*Petal reflex.*—Petals reflex slightly.

*Petal edge.*—Entire. Some petals with a point in center of margin.

*Petal shape.*—Apex shape is round. Shape of base is deltoid.

*Petal size.*—Variable. Petal sizes range are 40–45 mm long and 25–35 mm wide.

*Thickness.*—Thick.

*Petal arrangement.*—Informal to quartered in arrangement.

*Petaloids.*—Limited in numbers. Average of 5 per flower. Petaloids are 10 mm long and 3–4 mm wide. Color of inner side is Yellow-White Group 158C. Color of outer side is Yellow-White Group 158C. Surface texture is smooth. Shape is linear.

Reproductive organs:

*Pistils.*—Average. Approximately 40–45 present. Stigmas: Location: Superior in location to anthers. Color: Green-White Group 157A. Styles: Length: 15 mm long. Color: Green-White Group 157A.

*Stamens.*—Average 40–45 in number. Anthers: Size: 2–2½ mm long. Color: Yellow-Orange Group 16A. Pollen: Scant. Color: Greyed-Orange Group 164B. Filaments: Color: Green-Yellow Group 1C. Length: 3–6 mm.

THE PLANT

Plant growth: Moderate vigor. Upright to bushy. When grown as a budded nursery plant the average plant height is 80 cm and the average plant width is 75 cm.

Stems:

*Stem color.*—Young wood: Green Group 138A. Older wood: Green Group 138A.

*Stem surface.*—Young wood: Smooth. Older wood: Smooth.

Prickles: Present.

*Incidence.*—8–14 per 10 cm of stem.

*Size.*—Average length: 5–7 mm.

*Color.*—Juvenile prickles: Basal area with intonations of Greyed-Red Group 181C. Above, prickle is Greyed-Yellow Group160C. Mature prickles: Basal area with intonations of Greyed-Purple Group 183B. Above, prickle is Greyed-Orange Group 165D. On some mature prickles, the distal end has intonations of Greyed-Purple Group 183B.

*Shape.*—Deeply concave.

Leaves and leaflets: Normally 5 leaflets on normal leaves in middle of the stem.

*Leaf size.*—110 mm (l)×70 mm (w).

*Quantity.*—Abundant.

*Texture.*—Semi glossy to glossy. Smooth.

*Color, mature foliage.*—Upper Leaf Surface: Green Group 137A. Lower Leaf Surface: Green Group 138A.

*Color, juvenile foliage.*—Upper Leaf Surface: Green Group 137A. Lower Leaf Surface: Green Group 138A.

*Anthocyanin intonation.*—Absent.

Stipules:

*Size.*—10–16 mm (l)×5–6 mm (w).

*Stipule color.*—Green Group 144A.

*Presence of stipitate glands.*—Limited numbers present on margins.

*Margins.*—Bearded. Serrated.

Petiole:

*Length.*—5–15 mm.

*Diameter.*—1.5 mm.

*Petiole color.*—Green Group 138A.

*Prickles.*—A few small prickles underneath. Color Green Group 157A.

*Stipitate glands.*—Few to none on the margins.

Petiole rachis:

*Length.*—5–15 mm.

*Diameter.*—1.5 mm.

*Color.*—Green Group 138A.

*Prickles.*—Lacking. Surface generally smooth.

*Stipitate glands.*—Limited numbers on margins.

Leaflets:

*Size.*—Average size of the terminal leaflet is 40–45 mm (l)×30 mm(w).

*Shape.*—Ovate. Shape of base is obtuse. Shape of apex is acute.

*Margins.*—Serrated.

*Texture.*—Thick. Upper surface: Semi glossy to glossy. Smooth. Lower surface: Leathery.

Hips/seed formation: None observed.

Winter hardiness: To date, the variety has been grown successfully in Zone 5.

Disease resistance: Excellent resistance to Blackspot, mildew, and Botrytis diseases under normal growing conditions.

I claim:

1. A new and distinct variety of rose plant characterized by the following combination of characteristics:

(a) forms attractive, long lasting cream white flowers;

(b) exhibits uniform upright and bushy growth habit;

(c) propagates well using traditional methods, and;

(d) exhibits excellent resistance to disease under normal growing conditions;

substantially as herein illustrated and described.

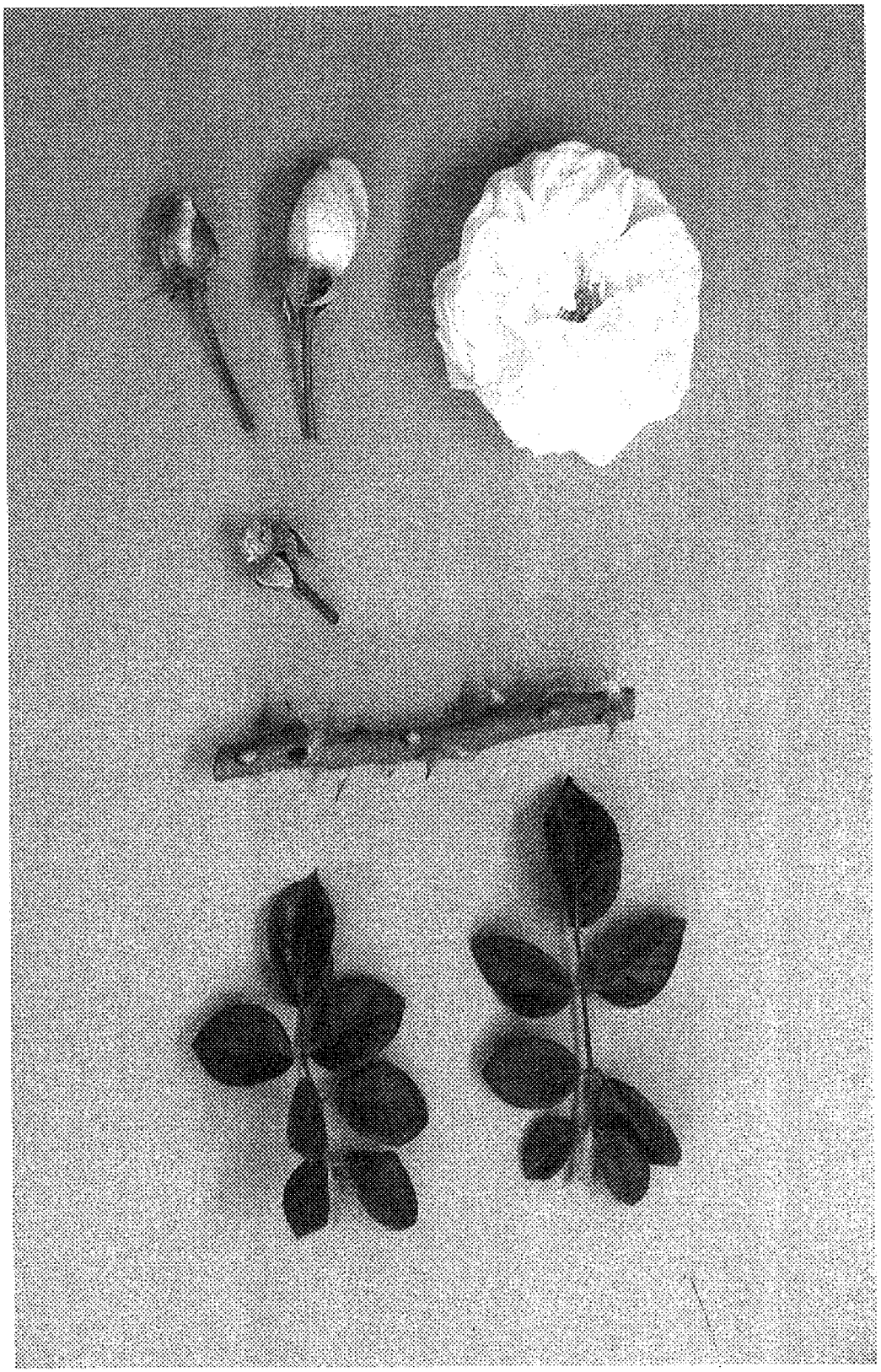

* * * * *